United States Patent
Lee et al.

(10) Patent No.: US 9,010,195 B2
(45) Date of Patent: Apr. 21, 2015

(54) APPARATUS FOR APPLYING HORIZONTAL LOAD TO UNDERWATER PILE USING GROUND PENETRATION OF SUCTION PILE AND METHOD FOR MEASURING HORIZONTAL RESISTANCE OF UNDERWATER PILE USING THE SAME

(71) Applicant: Korea Institute of Construction Technology, Goyang-si, Gyeonggi-do (KR)

(72) Inventors: Ju Hyung Lee, Paju-si (KR); Moon Kyung Chung, Seoul (KR); Ki Seok Kwak, Seoul (KR); Jae Hyun Park, Goyang-si (KR)

(73) Assignee: Korea Institute of Construction Technology, Goyang-si, Gyeonggi-do (KR)

( * ) Notice: Subject to any disclaimer, the term of this patent is extended or adjusted under 35 U.S.C. 154(b) by 0 days.

(21) Appl. No.: 14/224,937

(22) Filed: Mar. 25, 2014

(65) Prior Publication Data

US 2014/0290379 A1    Oct. 2, 2014

(30) Foreign Application Priority Data

Mar. 29, 2013    (KR) .................. 10-2013-0034654

(51) Int. Cl.
*G01N 3/08*    (2006.01)

(52) U.S. Cl.
CPC .......................................... *G01N 3/08* (2013.01)

(58) Field of Classification Search
CPC . G01N 3/08; B63B 21/502; E02B 2017/0043
USPC ...................... 73/826, 828, 862.393, 862.637
See application file for complete search history.

(56) References Cited

U.S. PATENT DOCUMENTS

| | | | |
|---|---|---|---|
| 4,388,710 A | * | 6/1983 | Pecon, Jr. ...................... 367/134 |
| 6,685,396 B1 | | 2/2004 | Bergeron |
| 8,087,464 B2 | * | 1/2012 | Rodrigues et al. ............. 166/339 |
| 2009/0232605 A1 | * | 9/2009 | Breivik ......................... 405/203 |
| 2012/0082514 A1 | * | 4/2012 | Horton et al. .................. 405/204 |
| 2012/0211234 A1 | * | 8/2012 | Wilie et al. .................... 166/345 |
| 2012/0315097 A1 | | 12/2012 | Paulus et al. |

FOREIGN PATENT DOCUMENTS

| | | |
|---|---|---|
| JP | 3722906 B2 | 11/2005 |
| KR | 10-2007-0101638 A | 10/2007 |
| KR | 10-2012-0137249 A | 12/2012 |
| KR | 10-1207199 B1 | 12/2012 |

* cited by examiner

*Primary Examiner* — Max Noori
(74) *Attorney, Agent, or Firm* — Fenwick & West LLP

(57) ABSTRACT

A horizontal resistance of an underwater pile is measured using a horizontal load applying apparatus which applies a horizontal load to the underwater pile to measure a horizontal resistance of the underwater pile by changing a direction of a penetration force generated when a suction pile penetrates an underwater ground.

7 Claims, 8 Drawing Sheets

APPARATUS FOR APPLYING HORIZONTAL LOAD TO UNDERWATER PILE USING GROUND PENETRATION OF SUCTION PILE AND METHOD FOR MEASURING HORIZONTAL RESISTANCE OF UNDERWATER PILE USING THE SAME

CROSS-REFERENCE TO RELATED APPLICATION

This application claims the benefit of Korean Patent Application No. 10-2013-0034654, filed on Mar. 29, 2013, which is incorporated by reference herein in its entirely.

BACKGROUND

1. Field

The present disclosure relates to an apparatus for applying a horizontal load to an underwater pile to measure a horizontal resistance of the underwater pile interpenetrating an underwater ground uprightly and a method for measuring a horizontal resistance of an underwater pile using the apparatus.

2. Description of the Related Art

When evaluating the performance of a pile installed on the ground vertically, it is very important to accurately measure the capacity of the pile to endure a horizontal load applied thereto, namely a horizontal resistance of the pile. In the case a pile is installed on the ground of the land, the horizontal resistance of the pile may be measured in various ways. However, the horizontal resistance measuring method applied to the land may not be easily applied to an underwater pile installed on the ground in water since a top of the underwater pile is located in water. In particular, since the underwater pile is located in a water stream such as tides or waves, the influence of such water stream and the depth of water should be put into consideration.

SUMMARY

Accordingly, the present disclosure is directed to a technique for measuring a horizontal resistance of an underwater pile installed on an underwater ground vertically in a stable and accurate way.

In detail, the present disclosure is directed to an apparatus for applying a horizontal load to an underwater pile to measure a horizontal resistance of the underwater pile by changing the direction of a penetration force generated by penetration of a suction pile into the underwater ground. In addition, the present disclosure is directed to a method for measuring a horizontal resistance of an underwater pile by using the horizontal load applying apparatus.

In the present disclosure, there is provided an apparatus for applying a horizontal load to an underwater pile to measure a horizontal resistance of the underwater pile, the apparatus including: a tension wire connected to an underwater pile of a measurement target; a suction pile for pulling the tension wire while penetrating the ground by suction; a member for changing a direction of the tensile force for pulling the tension wire into a horizontal direction; a support at which the direction changing member is installed; and a tensile force measurer for measuring the tensile force applied to the tension wire, wherein an operating direction of the tensile force applied to the tension wire downwards by ground penetration of the suction pile is changed by the direction changing member into a horizontal load with respect to the underwater pile.

In addition, in the present disclosure, there is also provided a method for measuring a horizontal resistance of an underwater pile by applying a horizontal load to the underwater pile by using the apparatus for applying a horizontal load as described above. In other words, the present disclosure provides a method for measuring a horizontal resistance of an underwater pile, which includes: installing a support having a direction changing member on the underwater ground; positioning a suction pile at the underwater ground so that the suction pile connected to the other end of a tension wire penetrates the underwater ground; and allowing the suction pile to penetrate the ground by suction to pull the tension wire, in a state where one end of the tension wire is connected to an underwater pile of a measurement target, wherein the tension wire is pulled in a state where the tension wire is supported by the direction changing member, so that an operating direction of a tensile force applied to the tension wire downwards by ground interpenetration of the suction pile is changed by the direction changing member into a horizontal load with respect to the underwater pile, and a tensile force applied to the tension wire is measured by the tensile force measurer to measure a horizontal resistance of the underwater pile.

In the apparatus and method of the present disclosure, the direction changing member may be configured with a pulley and installed at an upper surface of a support, and an opening may be formed through the support in a vertical direction so that the suction pile is inserted into the opening and penetrates the ground while being guided by the support. Further, a winch capable of winding the tension wire may be further provided at the suction pile.

In the present disclosure, a horizontal load is applied to an underwater pile to measure a horizontal resistance of the underwater pile by changing the direction of a penetration force generated by penetration of a suction pile into the underwater ground. In addition, a horizontal resistance of the underwater pile is measured by measuring a horizontal load applied to the underwater pile as described above.

In the present disclosure, since a horizontal load is applied to the underwater pile to measure its horizontal resistance and is generated by ground penetration of a suction pile, a water stream does not give any influence, and therefore it is possible to apply a uniform horizontal load to the underwater pile in a state of putting influences of tides, waves, wind or the like aside. Therefore, according to the present disclosure, it is possible to reliably measure a horizontal resistance of an underwater pile.

In addition, in the present disclosure, since the depth of water does not give a serious influence when applying a horizontal load to the underwater pile, the present disclosure may be easily implemented in shallow water.

In particular, since the penetrating speed and the penetration force of a suction pile into the ground may be precisely controlled using a pump (or, a motor), the horizontal load applied to the underwater pile may also be precisely controlled in the present disclosure.

Moreover, in the present disclosure, a direction changing member may be configured with a pulley, and a tensile force applied to a tension wire by penetration of a suction pile may be amplified by adjusting an arrangement of the pulley.

In addition, in the present disclosure, since the direction changing member is made of a heavy material such as concrete and installed at a support placed on the underwater ground, the direction changing member may be easily installed at a desired location regardless of the state of the ground, and the installation location may be stably fixed. In other words, in the present disclosure, the direction changing member may be stably placed at a desired location.

Moreover, in the present disclosure, the support may play a role of guiding penetration of the suction pile, and in this case, the suction pile may stably and easily penetrate the ground vertically.

BRIEF DESCRIPTION OF THE DRAWINGS

The above and other objects, aspects, features and advantages of the present invention will be more clearly understood from the following detailed description taken in conjunction with the accompanying drawings, in which.

DETAILED DESCRIPTION

Some exemplary embodiments of the present invention are described with reference to the accompanying drawings. The embodiments of the present invention are described with reference to the illustrated drawings, but are only illustrative, and the technical spirit, essential construction, and actions of the present invention are not restricted by the embodiments.

Figure 1:
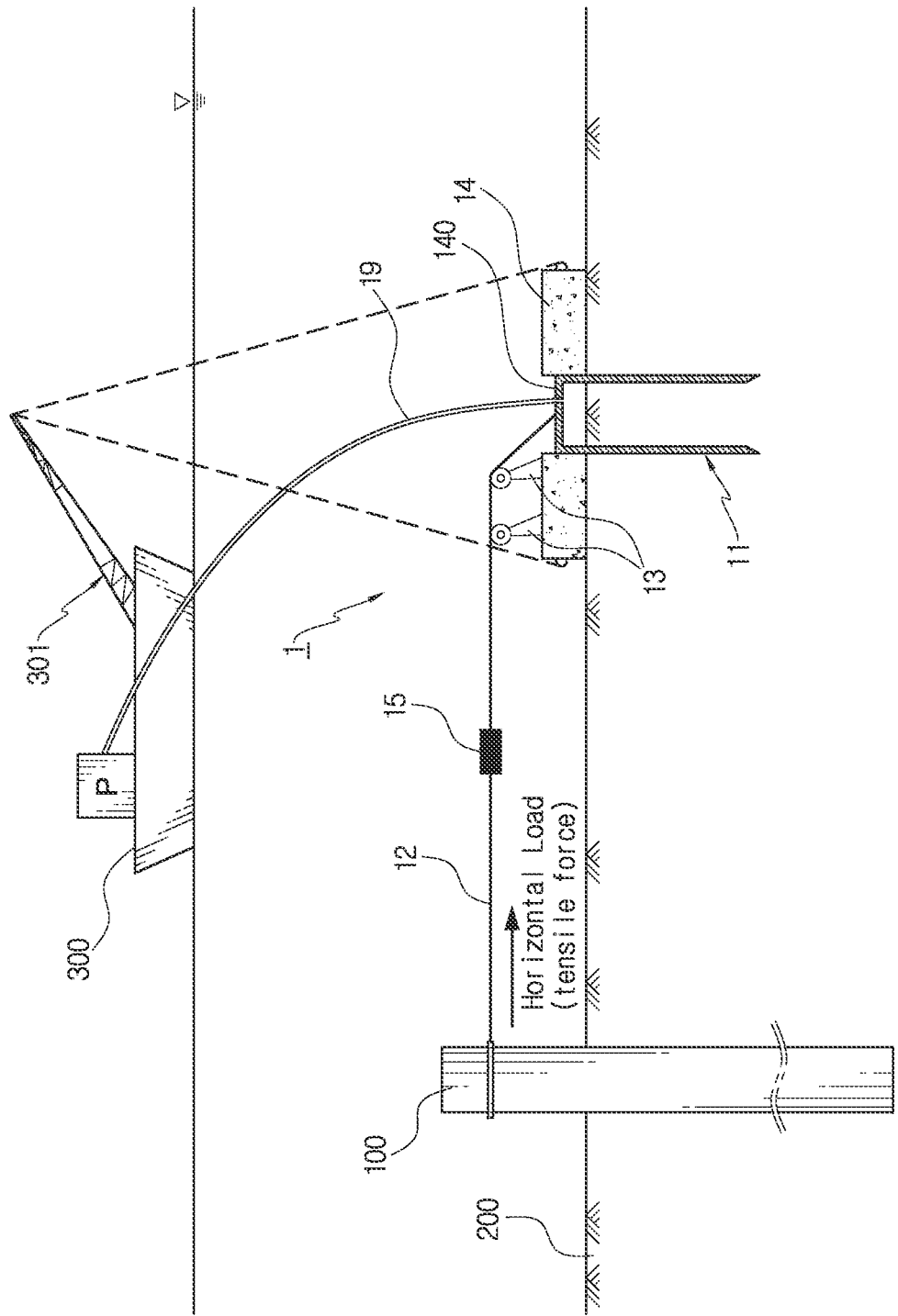
FIG. 1 is a side view showing a state of measuring a horizontal resistance of an underwater pile by using an apparatus for applying a horizontal load according to an embodiment of the present disclosure.

FIG. 1 is a schematic side view showing a state of measuring a horizontal resistance of an underwater pile by applying a horizontal load to the underwater pile with an apparatus for applying the horizontal load (hereinafter, also referred to as a "horizontal load applying apparatus") according to an embodiment of the present invention. The horizontal load applying apparatus 1 according to the present invention includes a tension wire 12 connected to an underwater pile 100 serving as a measurement target, a suction pile 11 for pulling the tension wire 12 while penetrating the ground by suction, a direction changing member 13 for changing a direction of the tensile force for pulling the tension wire 12 by the suction pile 11 into a horizontal direction, a support 14 at which the direction changing member 13 is installed, and a tensile force measurer 15 for measuring the tensile force applied to the tension wire 12.

One end of the tension wire 12 is coupled to the underwater pile 100 whose horizontal resistance is to be measured. In a state where the underwater pile 100 is vertically installed in the underwater ground 200, one end of the tension wire 12 is connected to the upper portion of the underwater pile 100 above the underwater ground 200. The other end of the tension wire 12 is coupled to the suction pile 11.

The tensile force measurer 15 measures a tensile force applied to the tension wire 12 and may be, for example, a load cell or the like. However, the tensile force measurer 15 may use various kinds and configurations, without being limited thereto. As shown in FIG. 1, the tensile force measurer 15 may be coupled to the tension wire 12, and its coupling position is not specially limited if the tensile force measurer 15 does not disturb the tension wire 12 being pulled.

The suction pile 11 is made of a pipe-shaped member having an open bottom and a closed top to have a hollow area therein. A drain pipe 19 is connected to the top of the suction pile 11. In a state where the bottom of the suction pile 11 contacts the ground, if the suction pile sucks the hollow area of the suction pile 11 through the drain pipe 19 to drain the water (together with air, if air coexists) filling the hollow area of the suction pile 11, a negative pressure is formed in the hollow area of the suction pile 11, and accordingly a downward penetration force is applied to the suction pile 11 by water pressure so that the suction pile 11 penetrates the underwater ground 200.

The other end of the tension wire 12 is connected to the suction pile 11. Therefore, if the suction pile 11 penetrates the underwater ground, the tension wire 12 is pulled, and accordingly a tensile force is applied to the tension wire 12. The tensile force is measured by the tensile force measurer 15.

The direction changing member 13 converts a direction of the tensile force by the suction pile 11 into a horizontal direction so that the tensile force generated when the suction pile 11 pulls the tension wire 12 may be applied as a horizontal load with respect to the underwater pile 100. The direction changing member 13 may be configured with, for example, a pulley installed at the upper surface of the support 14. As necessary, a plurality of direction changing members may be provided.

Figure 2:
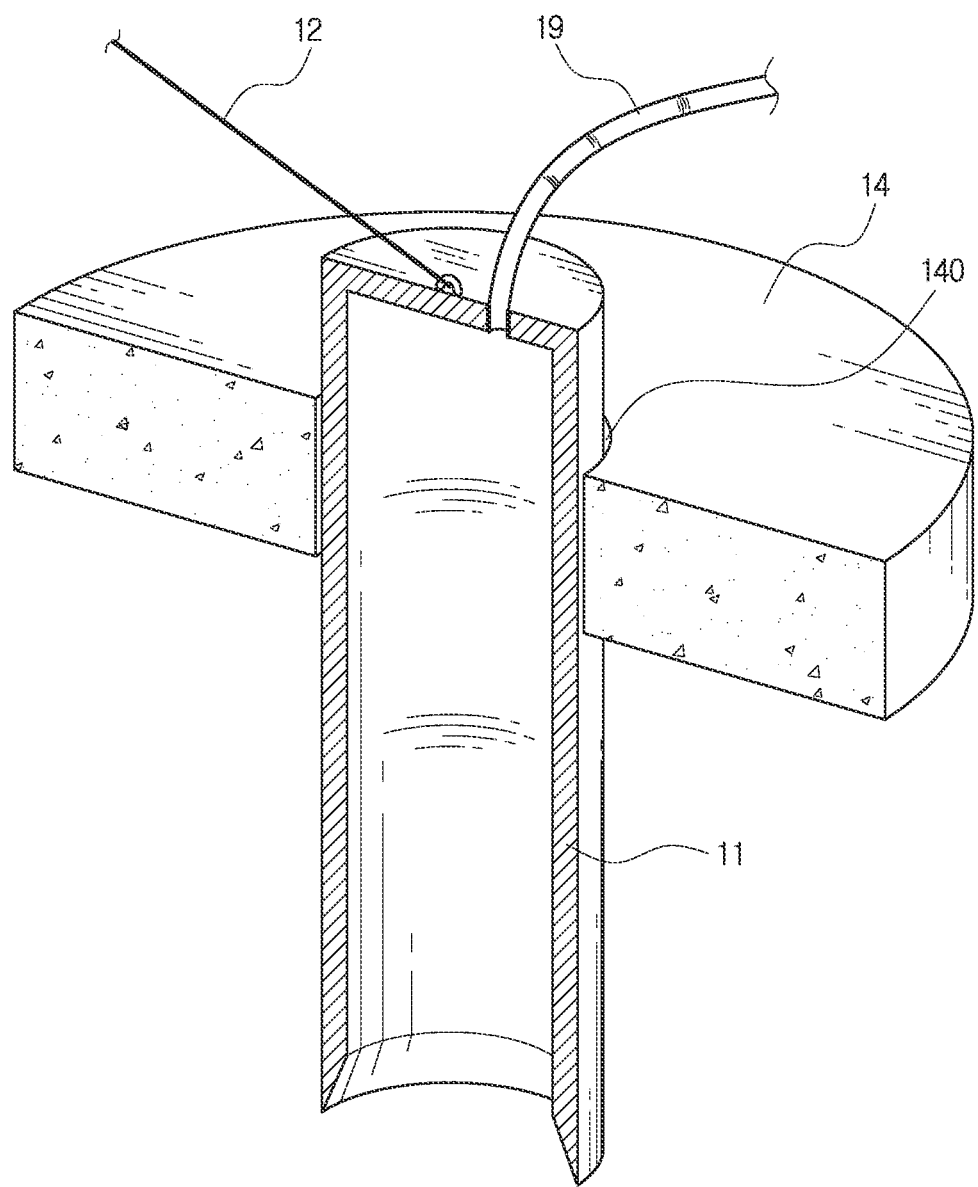
FIG. 2 is a half-sectional perspective view showing an example of a support employed in the present disclosure.

The support 14 is made of a heavy material such as concrete and placed on the underwater ground 200. The direction changing member 13 is installed at the support 14. Therefore, the direction changing member 13 may firmly fix its location without moving between the underwater pile 100 and the suction pile 11. In particular, in the embodiment depicted in FIG. 1, the support 14 additionally has a function of guiding the suction pile 11 to easily penetrate the underwater ground 200 in a vertical state. FIG. 2 is a half-sectional perspective view showing an example of the support 14 configured to guide the suction pile 11 to penetrate. As shown in FIG. 2, the support 14 may be fabricated to have a block shape in which a vertical opening 140 is formed. The suction pile 11 may penetrate the underwater ground 200 in a state of passing the opening 140 of the support 14 vertically. In other words, when the suction pile 11 penetrates the underwater ground 200, the suction pile 11 passes through the opening 140 of the support 14. Therefore, if the support 14 is in a horizontal state, the suction pile 11 is guided by the opening 140 vertically formed in the thickness direction of the support 14, and the suction pile 11 penetrates the underwater ground while automatically maintaining the upright state without shaking. Therefore, according to the embodiment of the present invention, the suction pile 11 may be installed to penetrate the underwater ground 200 in a very easy way. In FIG. 1, the reference symbol 300 represents a ship, and the reference symbol 301 represents lifting equipment used for holding or placing the support 14, the suction pile 11 or the like.

Figure 3:
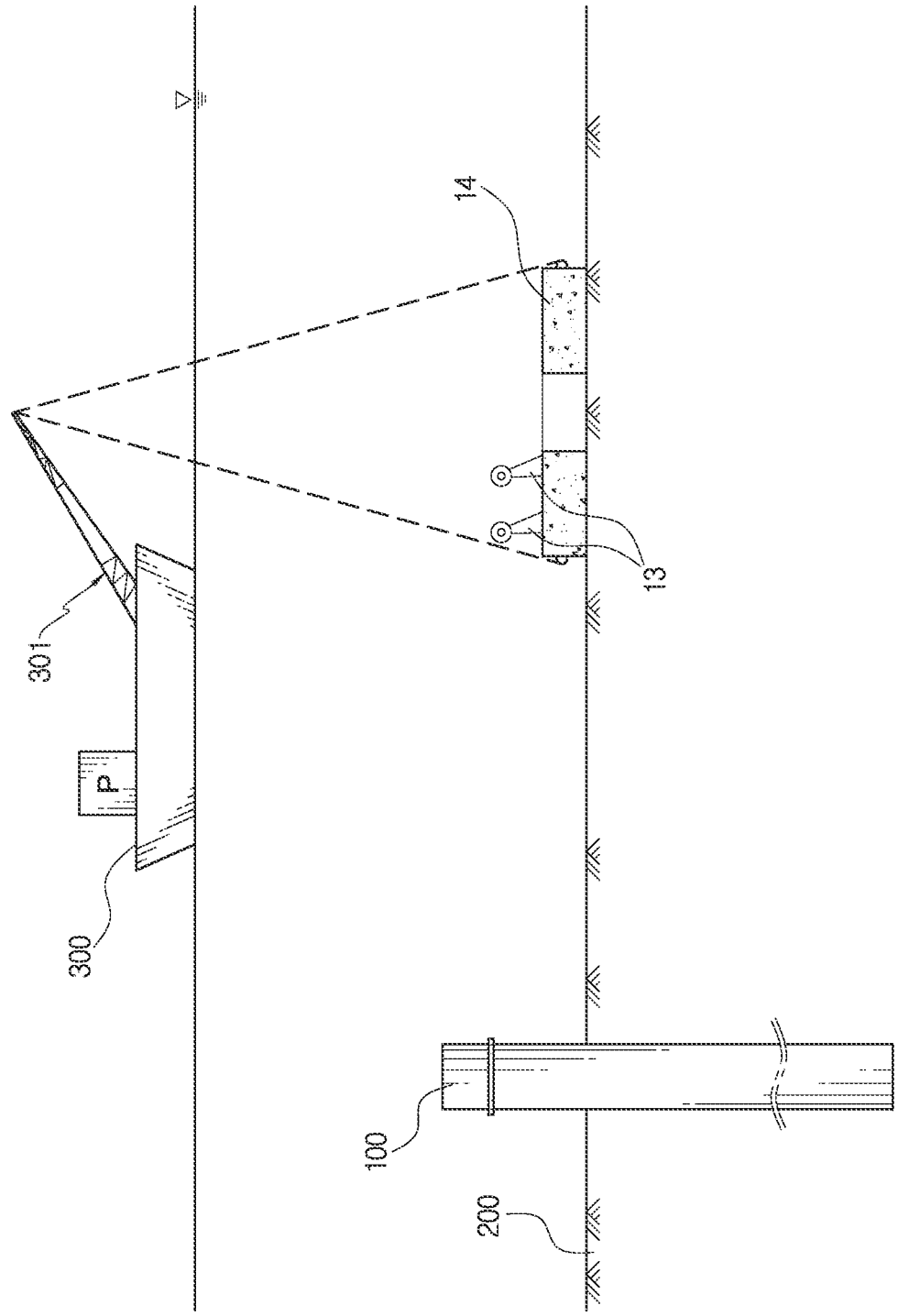
FIGS. 3 to 5 are respectively side views corresponding to FIG. 1 for illustrating processes of a method for measuring a horizontal resistance of an underwater pile according to the present disclosure in order.
Figure 4:
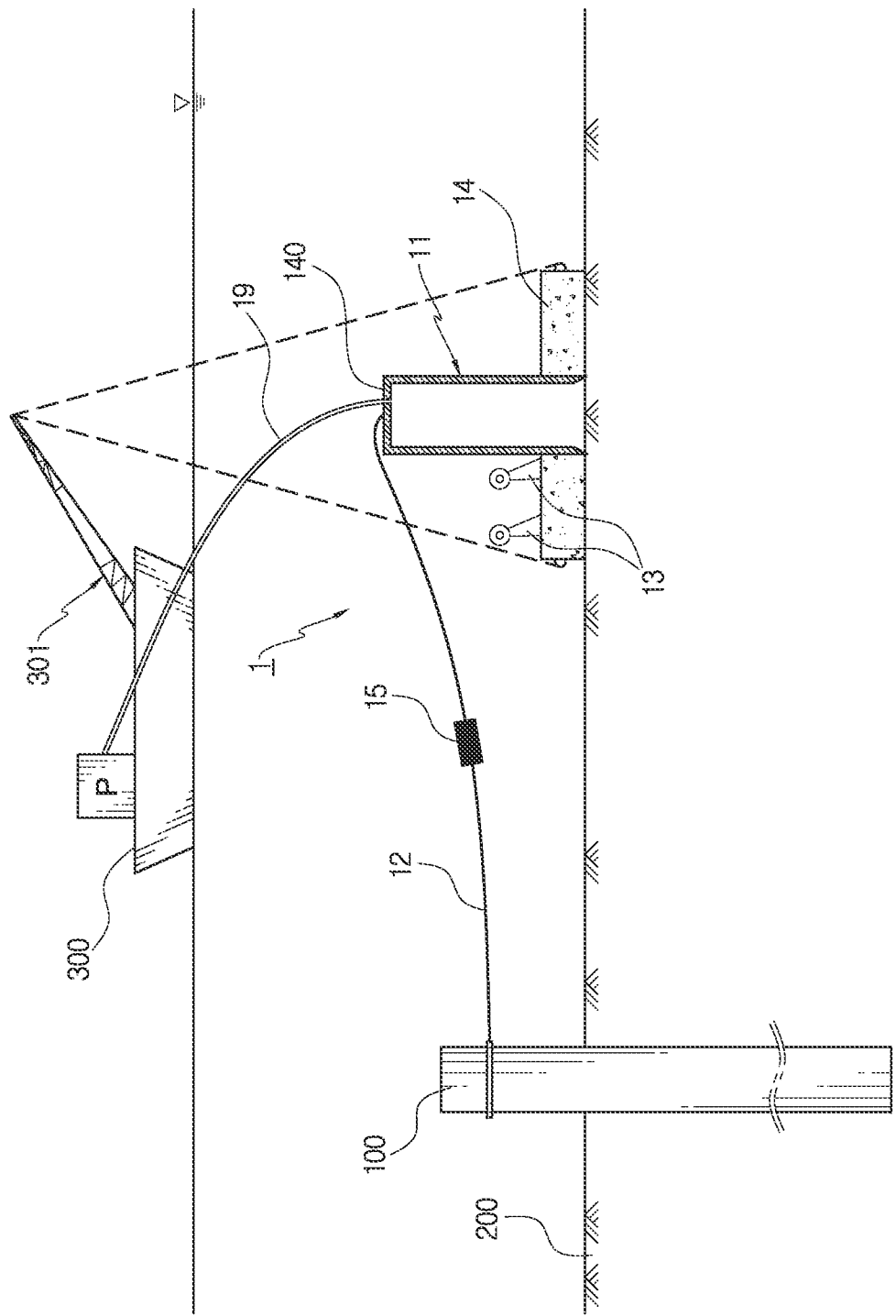
Figure 5:
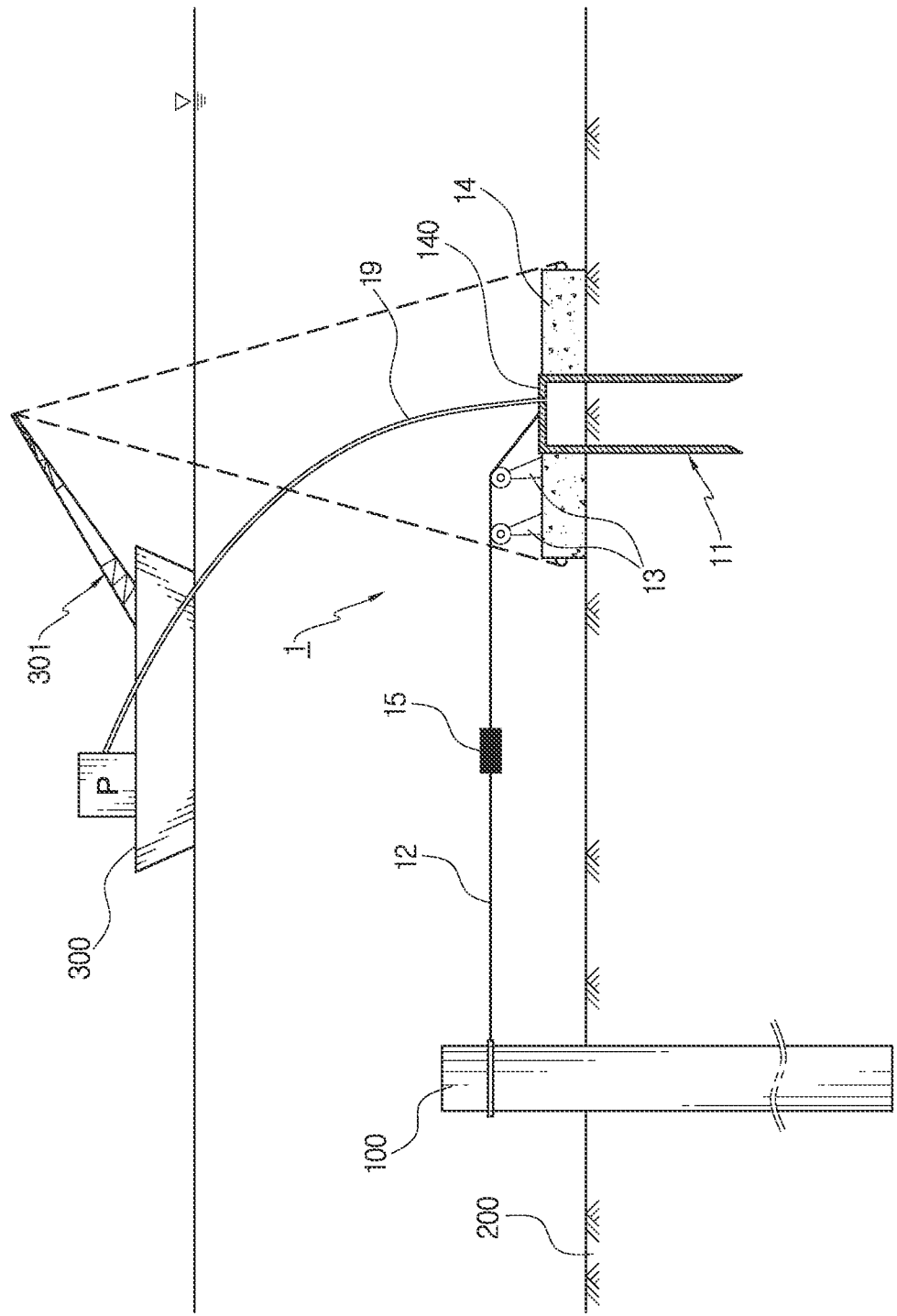

FIGS. 3 to 5 are schematic side views corresponding to FIG. 1, respectively. Hereinafter, processes of a method for measuring a horizontal resistance of an underwater pile according to the present disclosure will be described in order with reference to FIGS. 3 to 5. As shown in FIG. 3, near a place where the underwater pile 100 serving as a measurement target penetrates, the support 14 is placed on the underwater ground 200 by using the lifting equipment 301. After that, as shown in FIG. 4, the suction pile 11 coupled to the other end of the tension wire 12 interpenetrates the underwater ground 200. If the opening 140 is formed in the support 14 for guiding, the suction pile 11 passes through the opening 140 of the support 14 and its bottom contacts the underwater ground 200.

One end of the tension wire 12 is connected to the underwater pile 100. However, as shown in FIG. 4, before the suction pile 11 penetrates the underwater ground 200, a tensile force is not yet applied to the tension wire 12. When one end of the tension wire 12 is connected to the underwater pile 100, its position may be at the same height as the top of the direction changing member 13. In other words, when the support 14 is placed on the underwater ground 200, a location of one end of the tension wire 12 connected to the underwater pile 100 may be on the same horizontal line as the top of the direction changing member 13.

If a pump P installed at a ship or the like operates to vacuum the hollow of the suction pile 11 through the drain pipe 19, a negative pressure is formed in the inside space of the suction pile 11, and accordingly a downward penetration force is applied to the suction pile 11 by water pressure so that the suction pile 11 penetrates the underwater ground 200. FIG. 5 shows a state where the suction pile 11 is penetrating the underwater ground 200. The tension wire 12 is pulled by the penetration force of the suction pile 11, and a tensile force is applied to the tension wire 12.

FIG. 1 shows that the tension wire 12 is pulled after the state depicted in FIG. 5, and while the suction pile 11 is penetrating the underwater ground 200, the tension wire 12 is pulled in a penetration direction (a downward direction) of the suction pile 11. However, since the direction changing member 13 is located between the suction pile 11 and the underwater pile 100 and the direction changing member 13 supports the tension wire 12, the extension direction of the tension wire 12 is changed by the direction changing member 13. In particular, if a point where the direction changing member 13 supports the tension wire 12, namely a support point of the top of the direction changing member 13, is located on the same horizontal line as a position where one end of the tension wire 12 is coupled in the underwater pile 100, after the direction changing member 13, the tension wire 12 is in a horizontal state toward the underwater pile 100. Therefore, an operating direction of the tensile force applied downwards toward the other end of the tension wire 12 by the penetration of the suction pile 11 is converted by the direction changing member 13 so that the tensile force is applied in a horizontal direction with respect to the underwater pile 100. In other words, the tensile force generated at the tension wire 12 is applied as a horizontal load with respect to the underwater pile 100.

The horizontal load applied to the underwater pile 100 is measured by the tensile force measurer 15, and a horizontal displacement of the underwater pile 100 or an inclination of the underwater pile 100, generated by the horizontal load, is measured by a displacement meter or an angle meter.

In the present disclosure, the tension wire 12 is pulled by the penetration force generated while the suction pile 11 is penetrating the underwater ground 200 so that a tensile force is generated at the tension wire 12, and the tensile force is converted into a horizontal force by the direction changing member 13 to serve as a horizontal load with respect to the underwater pile 100. In addition, if the horizontal load is measured by the tensile force measurer 15, it is possible to figure out a horizontal resistance of the underwater pile 100. For example, by measuring the horizontal load applied to the underwater pile 100 until a horizontal displacement of the underwater pile 100 or an inclination of the underwater pile 100 reaches a preset value, the horizontal resistance of the underwater pile 100 may be measured by considering the measured horizontal load as the horizontal resistance of the underwater pile 100.

In particular, in the present disclosure, since the horizontal load applied to the underwater pile 100 to measure the horizontal resistance of the underwater pile 100 is generated by the ground penetration of the suction pile 11, the water stream does not give any influence. In other words, even though the water stream is under the influence of tides or wind, no influence is given to the horizontal load applied to the underwater pile 100. Therefore, in the present disclosure, it is possible to apply a uniform horizontal load to the underwater pile 100 while ruling out the influences by tides, waves, wind or the like, and accordingly, the horizontal resistance of the underwater pile 100 may be reliably measured.

In addition, since the depth of water does not give a serious influence when applying a horizontal load to the underwater pile 100, the present disclosure may be easily implemented in shallow water. Further, since the penetrating speed and the penetration force of the suction pile 11 into the ground may be precisely controlled using a pump P, the horizontal load applied to the underwater pile 100 may also be precisely controlled. In particular, the direction changing member 13 may be configured with a pulley, and a tensile force applied to the tension wire 12 by penetration of the suction pile 11 may be amplified by adjusting the arrangement of the pulley.

In the present disclosure, the direction changing member 13 is made of a heavy material such as concrete and installed at the support 14 placed on the underwater ground. Therefore, the direction changing member 13 may be easily installed at a desired location regardless of the state of the ground, and the installation location may be stably fixed. In other words, in the present disclosure, the direction changing member 13 may be stably positioned at a desired location.

In addition, if the opening 140 is formed in the support 14 in a vertical direction and the suction pile 11 penetrates the ground through the opening 140, the support 14 may play a role of guiding penetration of the suction pile 11, so that the suction pile 11 may stably and easily penetrate the ground vertically.

Figure 6:
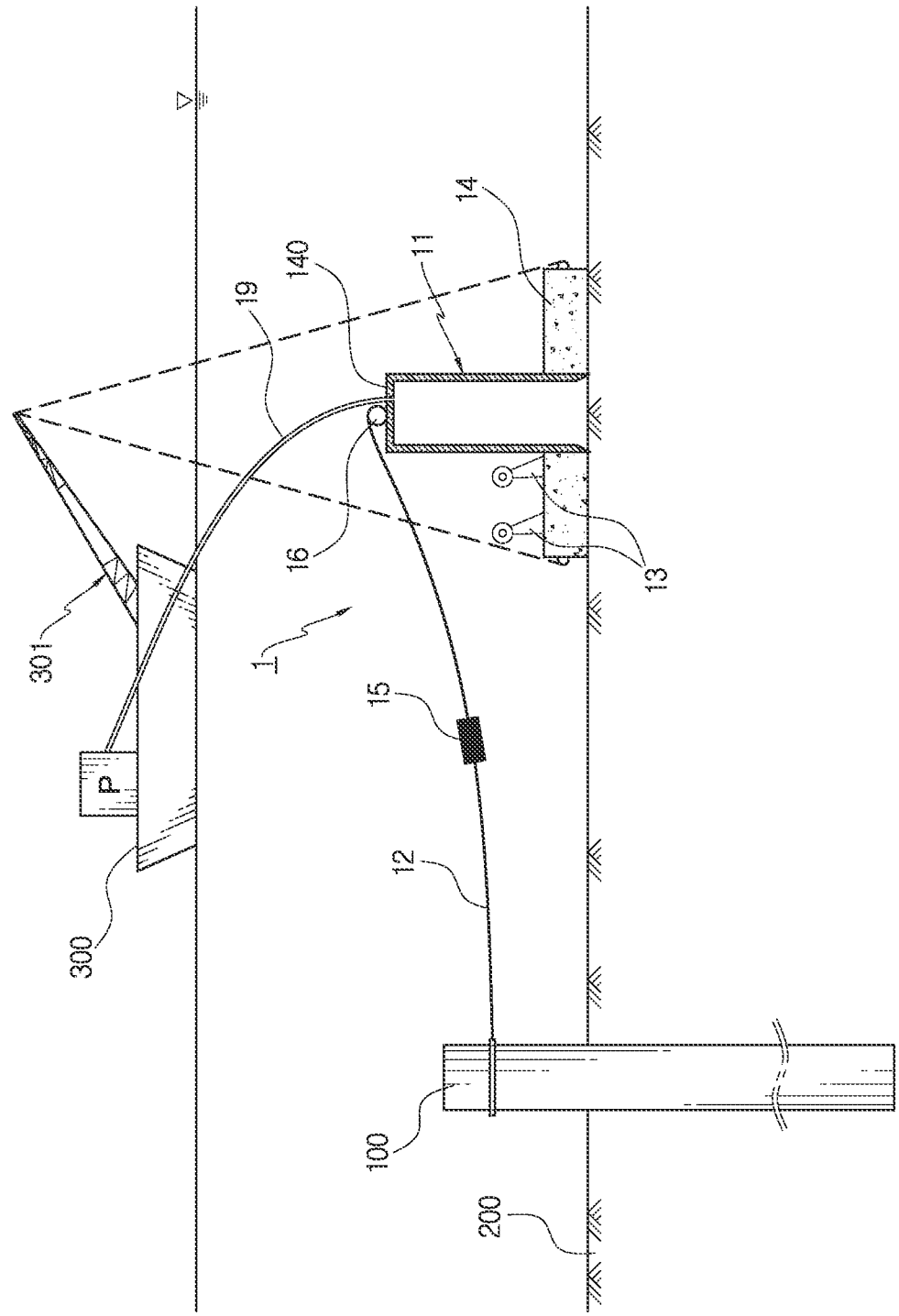
FIGS. 6 to 8 are side views showing another embodiment of the present disclosure having a winch.
Figure 7:
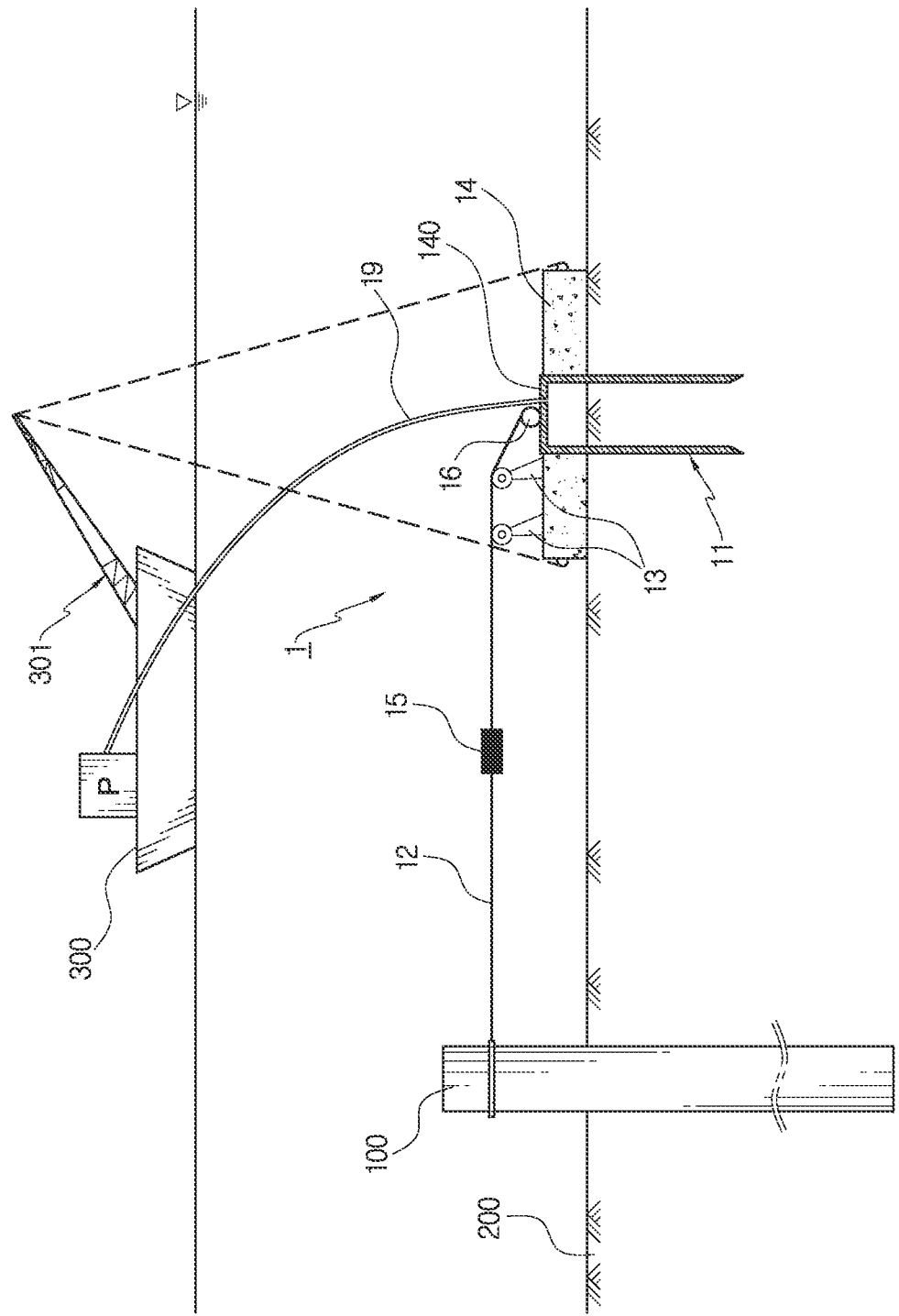
Figure 8:
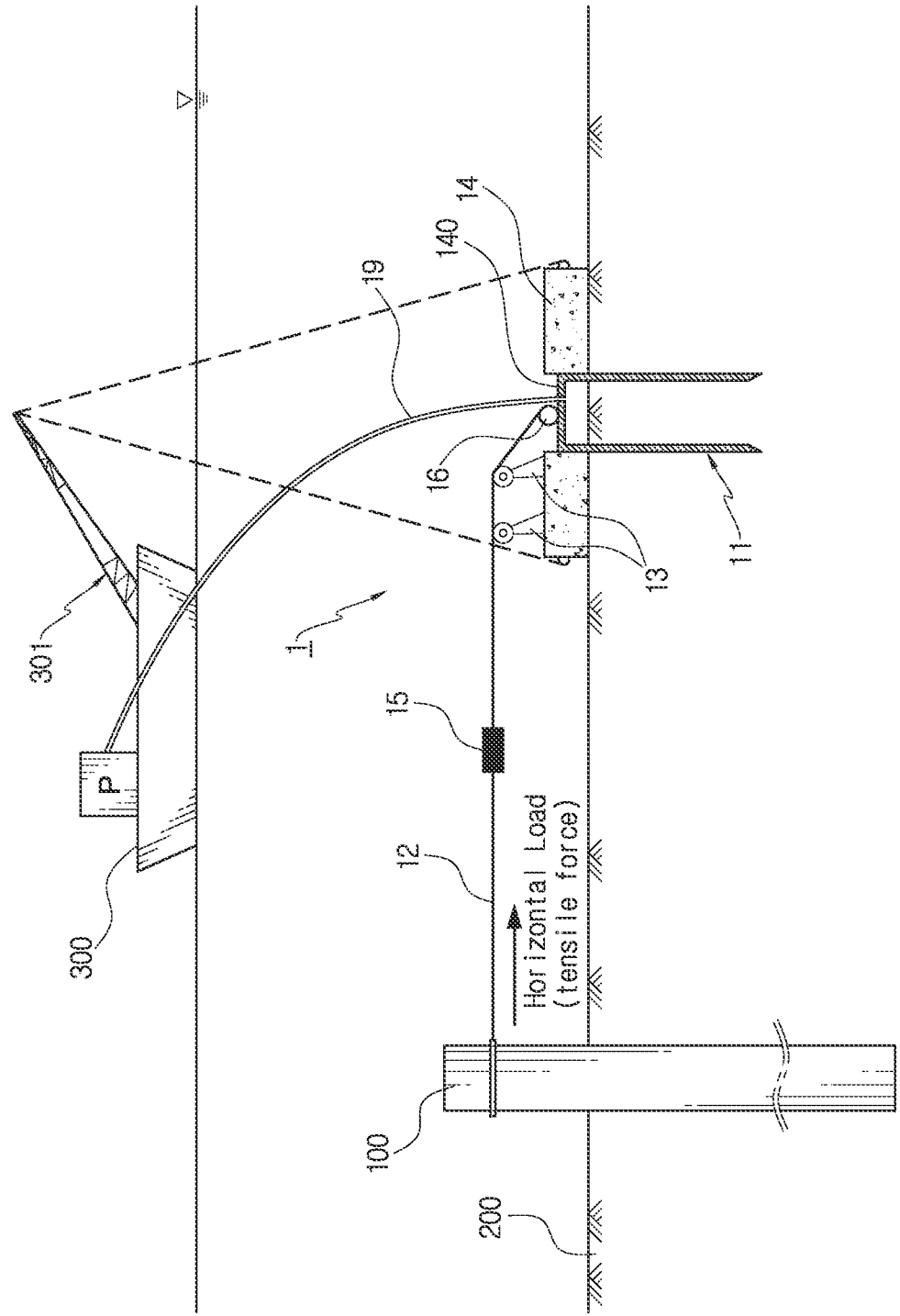

In the present disclosure, a winch 16 for winding the tension wire 12 may be further provided as necessary. FIGS. 6 to 8 are diagrams showing another embodiment of the present disclosure having a winch. FIG. 6 corresponds to FIG. 4, FIG. 7 corresponds to FIG. 5, and FIG. 8 corresponds to FIG. 1.

As shown in FIGS. 6 to 8, in the present disclosure, the winch 16 for winding the tension wire 12 may be further provided as necessary. In the case of FIGS. 6 to 8, the winch 16 is installed at the top of the suction pile 11. However, the installation location of the winch 16 is not limited thereto. If the winch 16 is installed, as shown in FIG. 6, even though the suction pile 11 does not yet penetrate the ground, the winch 16 may wind the tension wire 12 so that the tension wire 12 cannot be slack but is supported by the direction changing member 13. Therefore, it is possible to solve any convenience in work caused by the slack of the tension wire 12. In addition, if the ground penetration of the suction pile 11 is not smooth or sufficient so that the tensile force pulling the tension wire 12 is weak, an additional tensile force may be further applied if the winch 16 winds the tension wire 12. Therefore, the horizontal resistance of the underwater pile 100 may be measured without any problem.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for applying a horizontal load to an underwater pile to measure a horizontal resistance of the underwater pile, the apparatus comprising:
   a tension wire connected to an underwater pile of a measurement target;
   a suction pile for pulling the tension wire while penetrating the underwater ground by suction;
   a direction changing member for changing a direction of the tensile force for pulling the tension wire in a horizontal direction;
   a support at which the direction changing member is installed; and
   a tensile force measurer for measuring the tensile force applied to the tension wire,
   wherein an operating direction of the tensile force applied to the tension wire downwards by ground penetration of the suction pile is changed by the direction changing member into a horizontal load with respect to the underwater pile.

2. The apparatus as set forth in claim 1, wherein the direction changing member is configured with a pulley and installed at an upper surface of the support.

3. The apparatus as set forth in claim 1, wherein;
   an opening is formed through the support in a vertical direction; and
   the suction pile is inserted into the opening and penetrates the ground while being guided by the support.

4. The apparatus as set forth in claim 1, wherein a winch capable of winding the tension wire is further provided at the suction pile.

5. A method for measuring a horizontal resistance of an underwater pile, the method comprising the steps of:
   installing a support having a direction changing member on an underwater ground;
   positioning a suction pile at the underwater ground so that the suction pile connected to the other end of a tension wire penetrates the underwater ground; and
   allowing the suction pile to penetrate the ground by suction to pull the tension wire, in a state where one end of the tension wire is connected to an underwater pile of a measurement target,
   wherein the tension wire is pulled in a state where the tension wire is supported by the direction changing member, so that an operating direction of a tensile force applied to the tension wire downwards by ground penetration of the suction pile is changed by the direction changing member into a horizontal load with respect to the underwater pile, and a tensile force applied to the tension wire is measured by the tensile force measurer to measure a horizontal resistance of the underwater pile.

6. The method as set forth in claim 5, wherein the direction changing member is configured with a pulley and installed at an upper surface of a support.

7. The method as set forth in claim 5, wherein;
   an opening is formed through the support in a vertical direction, and
   the suction pile is inserted into the opening and penetrates the ground while being guided by the support.

* * * * *